United States Patent [19]

Livingston

[11] Patent Number: 4,487,072

[45] Date of Patent: Dec. 11, 1984

[54] ULTRASONIC TESTING OF TUBULAR GOODS

[76] Inventor: Waylon A. Livingston, 770 W. Rock Creek Rd., Norman, Okla. 73069

[21] Appl. No.: 407,295

[22] Filed: Aug. 11, 1982

[51] Int. Cl.³ ............................................. G01N 29/04
[52] U.S. Cl. ........................................ 73/622; 73/628
[58] Field of Search ................. 73/622, 628, 637, 638, 73/640, 641

[56] References Cited

U.S. PATENT DOCUMENTS

| | | | |
|---|---|---|---|
| 4,041,773 | 8/1977 | Hauldren et al. | 73/638 |
| 4,217,782 | 8/1980 | Pont | 73/637 |
| 4,375,165 | 1/1983 | de Sterke | 73/637 |
| 4,404,853 | 9/1983 | Livingston | 73/622 |

FOREIGN PATENT DOCUMENTS

| | | | |
|---|---|---|---|
| 2806550 | 8/1979 | Fed. Rep. of Germany | 73/622 |
| 2027199 | 2/1980 | Fed. Rep. of Germany | 73/622 |
| 1400484 | 4/1965 | France | 73/622 |
| 52-53486 | 4/1977 | Japan | 73/637 |

*Primary Examiner*—Anthony V. Ciarlante
*Attorney, Agent, or Firm*—Robert M. Hessin

[57] ABSTRACT

Method and apparatus for ultrasonic flaw inspection of non-rotating tubular goods. The apparatus includes a test head with circumferential arrays of transducers oriented for inspection for each of transverse, longitudinal and wall thickness defects, and the test head includes individual pulser and pre-amplifier arrays as sequentially controlled from a remotely disposed operator console. The console includes sequential signal processing circuitry for developing and displaying defect indications for the test specimen as it is moved longitudinally through the test head.

18 Claims, 9 Drawing Figures

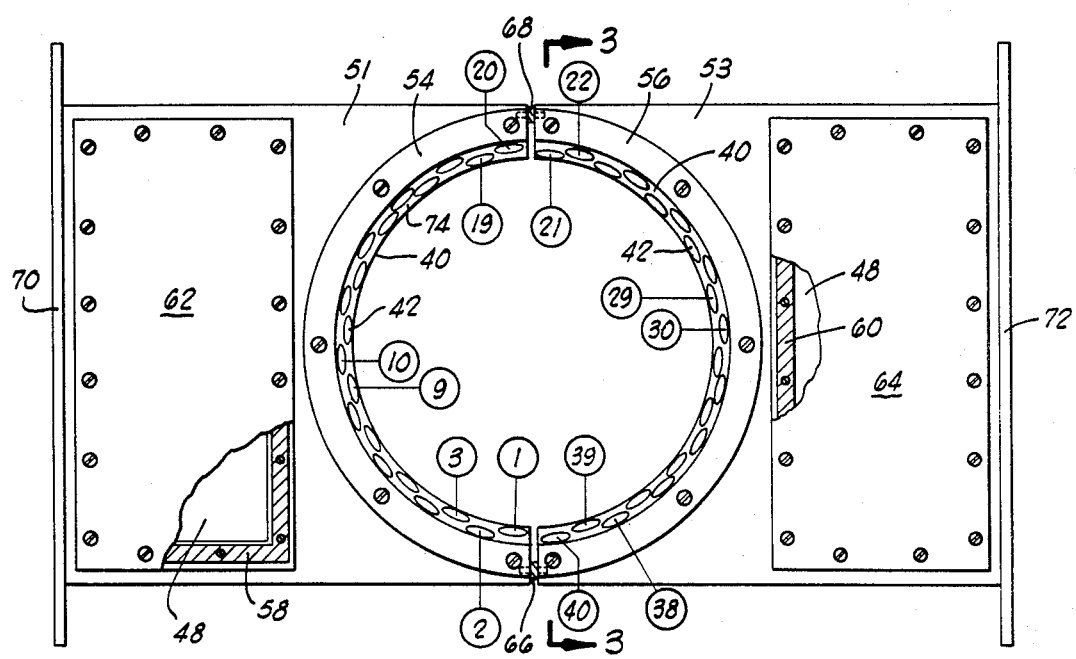
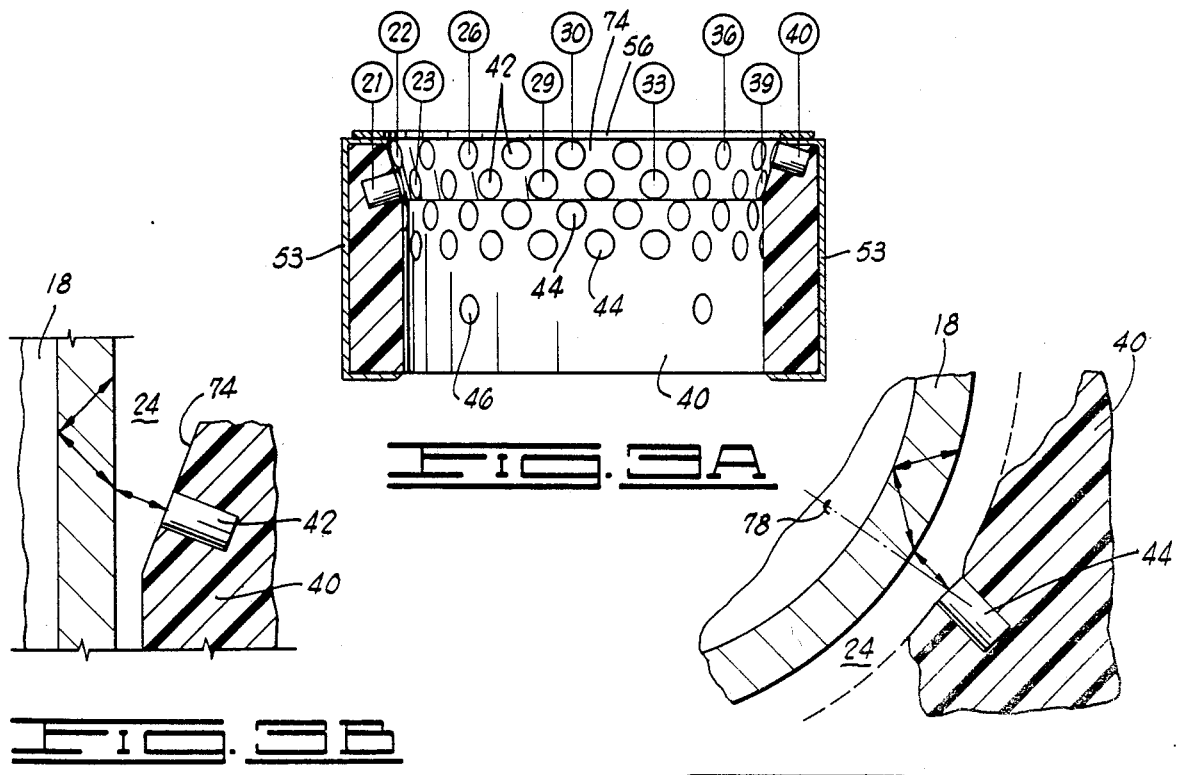

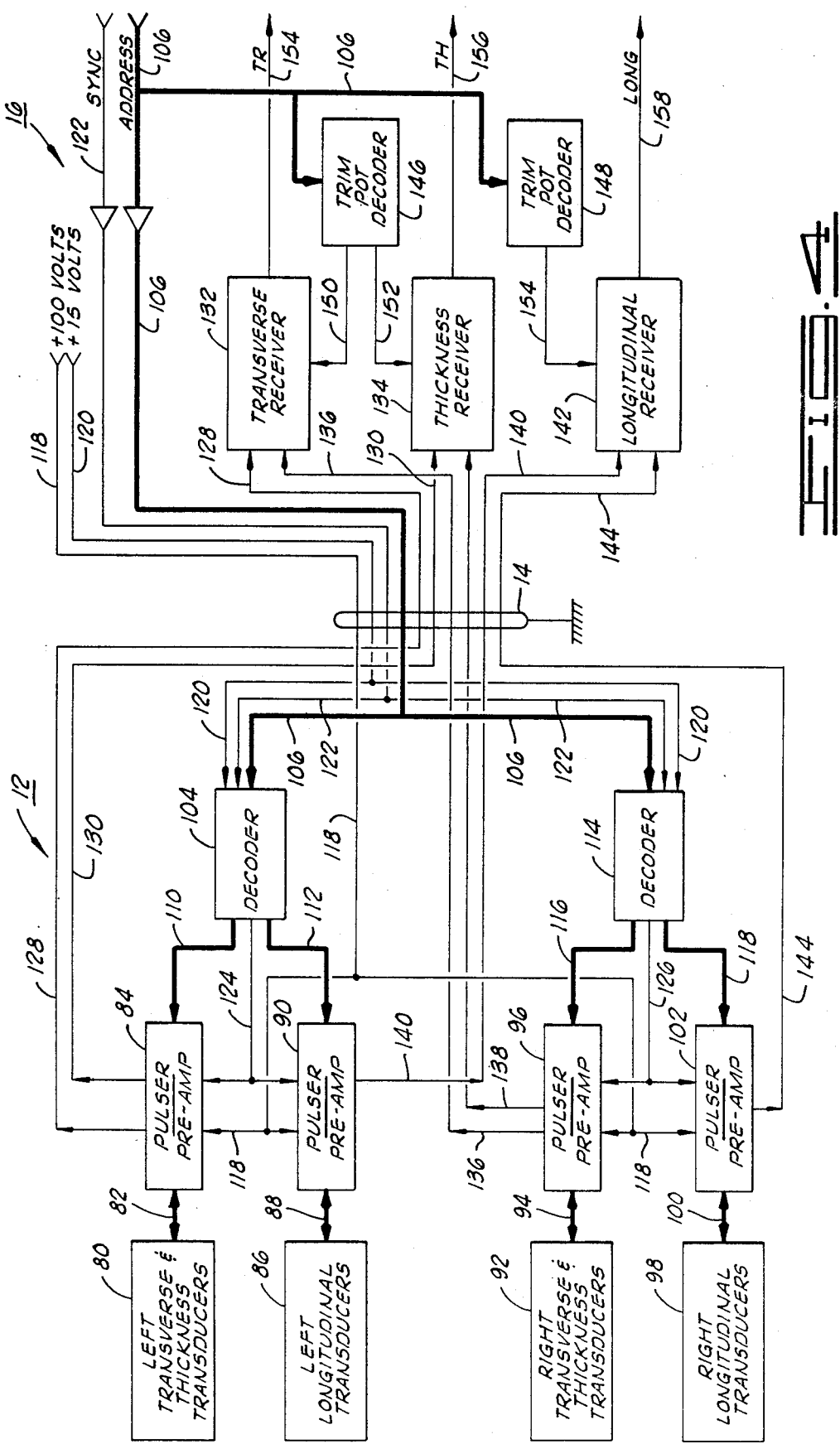

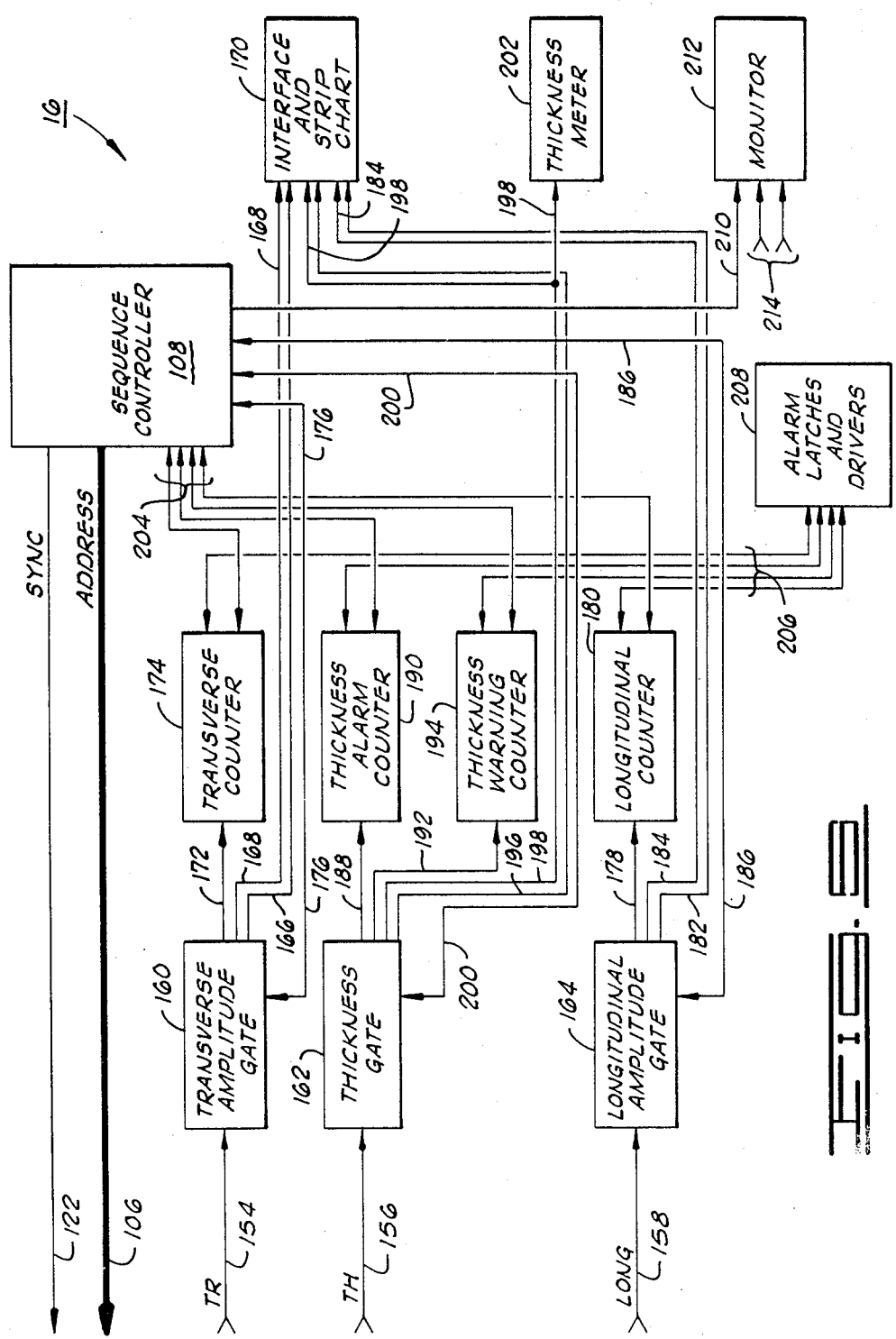

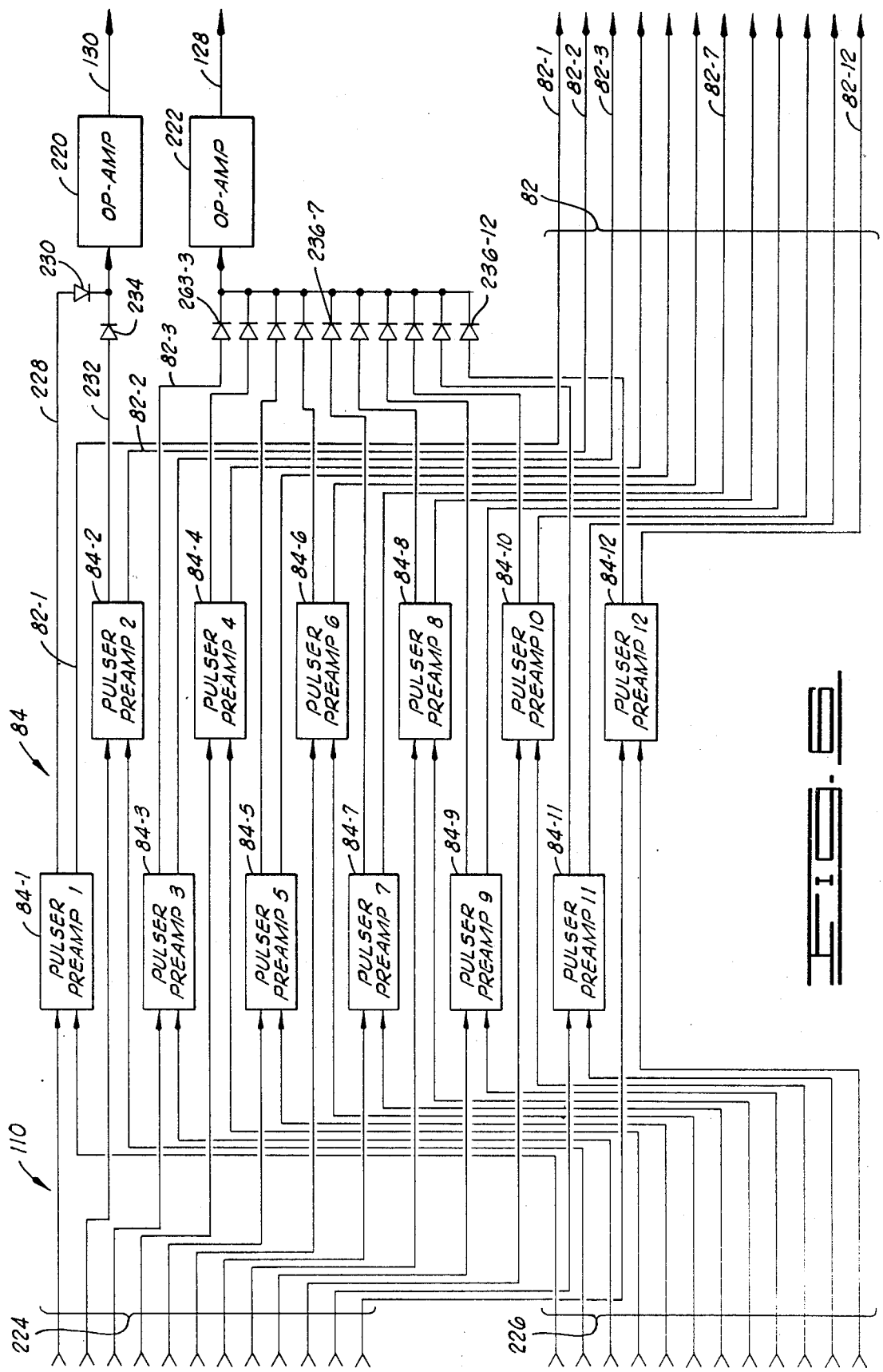

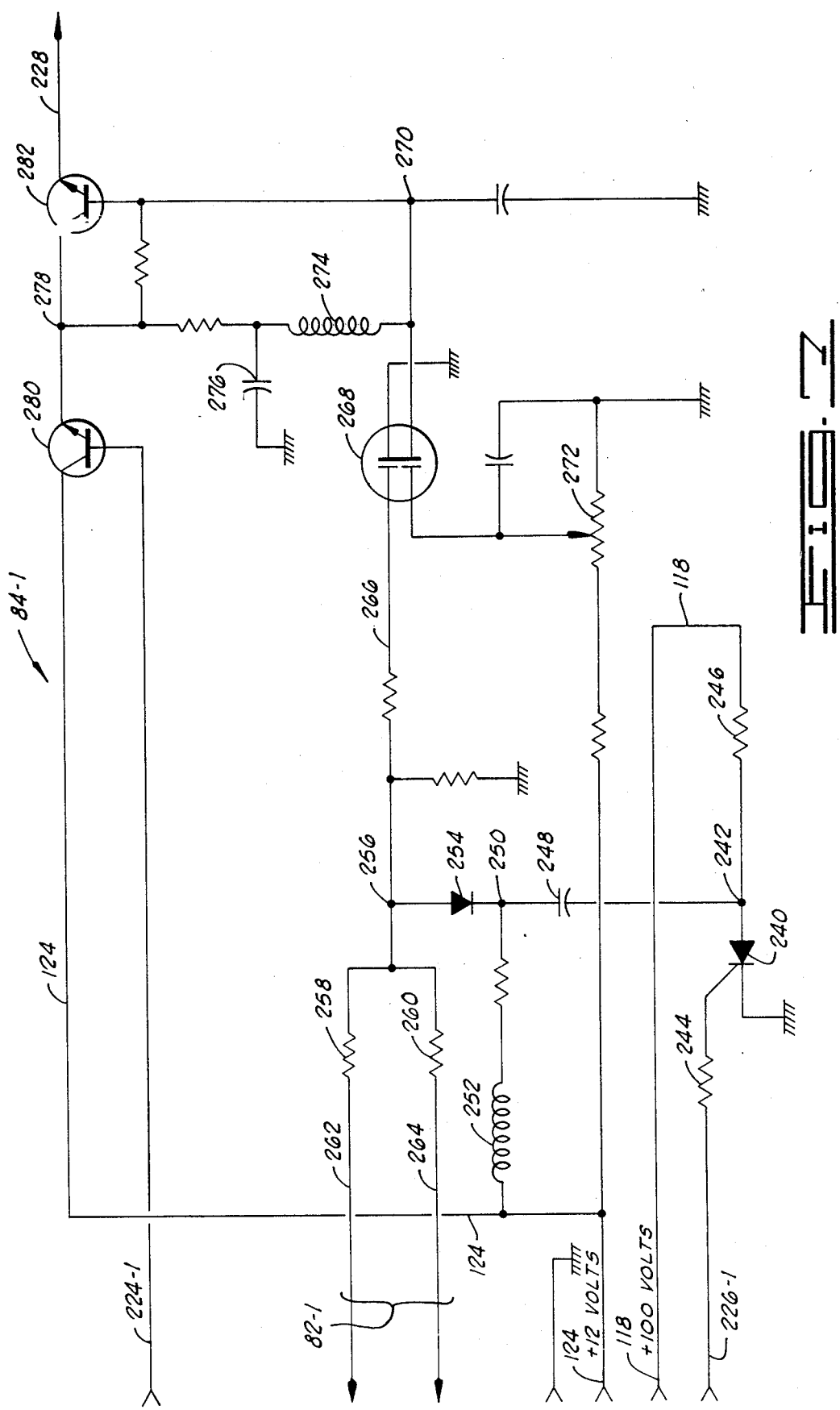

ULTRASONIC TESTING OF TUBULAR GOODS

BACKGROUND OF THE INVENTION

1. Field of the Invention

The present invention relates to improvements in method and apparatus for ultrasonic testing of tubular goods to determine defects, defect orientation and continuity, as well as wall thickness and, more particularly, but not by way of limitation, it relates to improvements in ultrasonic inspection apparatus which enables continuous circumferential testing without rotation of the tubular goods specimen.

2. Description of the Prior Art

The prior art includes various types of apparatus for ultrasonic testing of homogenous material, sheet or rod stock, with some more recent developments attempting such as continuous surface inspection of tubular goods. In most prior art attempts at ultrasonic inspection of tubular goods, it has been necessary to rotate the tubular goods specimen at a prescribed rate relative to its longitudinal movement past ultrasonic testing heads in order to provide complete and reliable surface coverage of the specimen wall or body. Most recently, there have been attempts at full and complete ultrasonic testing of tubular goods at acceptable linear inspection rates without requiring rotation of the specimen. U.S. patent application Ser. No. 242,833 as filed on Mar. 12, 1981 now U.S. Pat. No. 4,404,853 and entitled "Method and Apparatus for Ultrasonic Testing of Tubular Goods" in the name of the present inventor, discloses one form of circumferential testing apparatus wherein each of transverse and longitudinal defects can be ascertained, and periodic wall thickness measurement may be taken as well. The apparatus of U.S. application Ser. No. 242,833 is particularly adapted for on-site inspection of oil well drilling tubular goods during its tripping or vertical attitudes, although the same system is readily adapted for various horizontal testing applications in either field operational or manufacturing facilities.

Other prior art to be considered should include German Pat. No. 28 06 550 as filed on Feb. 16, 1978 as this reference teaches an approach to circumferential ultrasonic inspection utilizing a peripheral alignment of plural ultrasonic sensors with each having sufficient arcuate coverage to provide complete circumferential coverage of the tubular specimen. This is achieved by using two peripheral transducer arrays of equal sectoral coverage but staggered in an equal offset alternating relationship. The pair of arrays may be disposed adjacent one another, but each transducer array must be individually adjusted through a transducer lens and positioning device relative to the particular tubular goods specimen. If both transverse and longitudinal defect detection is desired, then it is necessary to align and adjust a separate pair of circumferential arrays for each of the selected defect characteristics. This reference contemplates no specific electronic apparatus for futher differentiating types of defects or for wall thickness considerations.

British Pat. No. 2,027,199 (A) teaches the use of a number of precision ground convex ancillary lenses that are each focused in a highly restricted area. Pairs of transducers with lenses may be used in a pitch-catch mode such that a greater number of transducers are required to provide complete circumferential coverage. The specific teaching of the patent for testing up to 10 centimeter tube diameters uses six pitch/catch transducers in a peripheral array, and at least four such peripheral arrays are aligned in longitudinal juxtaposition but incrementally circumferentially offset each to the other in order to provide complete coverage. While mention is made that transverse defects and wall thickness measurements are possible, no teaching or alternative suggestions are present. Finally, yet another pitch/catch mode of circumferential tubular goods inspection is present in a publication entitled "A High-Speed Ultrasonic Testing Machine for Tubes", The Radio and Electronic Engineer, Volume 41, No. 5, May 1971, in the name of Kyte and Whittington. This teaching uses a series of identical probes arranged in a ring encircling the tubular goods, each individual energy path including a transmitter and receiver position, and fast sequential pulsing of the probes together with slow rotation of the tube will enable effective circumferential scanning. This teaching contemplates both twin-probe or pitch/catch mode and the transceiver mode of operation but there is still required the rotation of the tubular specimen, albeit at a slow rate. Also, utilizing the disclosed forms of array, it is emphasized that the outer limit of ultrasonic transducer employment in the single system would be less than 72, and that the largest tube size for practical application of testing is less than four inches outside diameter.

SUMMARY OF THE INVENTION

The present invention relates to improvements in ultrasonic inspection of tubular goods and is particularly directed to a full coverage transducer collar for longitudinal, transverse and thickness testing to provide a more definitive and more reliable readout of defect type and orientation, and the invention is particularly adapted for use on-site during vertical tripping and pipe handling operations to test oil well drilling tubular goods. The apparatus consists of a circumferential transducer array operative within a couplant bath at the tubular goods inspection site. Individual pulser and pre-amp circuitry is retained in water proof enclosure in close proximity at the testing site while the entire test head unit is connected by a multi-conductor umbilical cable to an operator control position and control console which may be located at a considerable distance. The test head unit transducers are sequentially pulsed singly or in selected groups for each of the transverse, longitudinal and thickness testing transducers and each, in turn, provides a sequential RF signal output pre-amplied for transmission to the control console. The control console includes an individual receiver and decoder for each of the longitudinal, transverse and thickness RF signals as each provides a video output signal to a respective gate circuit which further provides output to a respective averager circuit for alarm output. Each circuit output is also applied from the individual gates to a strip chart or other output recorder. Coordination of the signal multiplexing as between the individual transducer pulsing and output sequences is carried out by a microprocessor circuit having buss connection both to the receiver and decoder circuits and the pulser and preamp circuits within the test head unit.

Therefore, it is an object of the present invention to provide an ultrasonic testing device for non-rotated tubular goods which provides more complete and reliable tube wall surface coverage to ascertain each of transverse and longitudinal defects as well as wall thickness.

It is also an object of the present invention to provide an ultrasonic tester having the capability of distinguishing the size and orientation of defects.

It is still further an object of the present invention to provide an ultrasonic tester which is rig-safe and operative in hazardous environment as all pulser/pre-amp components and transducer interconnection are immersed within couplant bath at the testing site.

It is yet another object of the present invention to provide an ultrasonic test head for extended surface coverage which is capable of being located at considerable distances from the main control console without deleterious effects.

It is also an object of this invention to provide a circular array of testing transducers which provide full circumferential coverage of tubular goods within widely varying diametric limits without individual transducer or array adjustment.

Finally, it is an object of the present invention to provide an electronic multiplexing and processing system for use in ultrasonic testing of tubular goods which is maximum effective yet extremely rugged and of high reliability in operation in difficult environs such as those of an oil well drilling rig.

Other objects and advantages of the invention will be evident from the following detailed description when read in conjunction with the accompanying drawings which illustrate the invention.

BRIEF DESCRIPTION OF THE DRAWINGS

FIG. 2 is a top plan view of the test head unit with parts shown in cutaway;

FIG. 3A is a vertical section of the transducer array as taken through lines 3—3 of FIG. 2;

FIG. 3B is a view in partial vertical section of a transverse defect transducer within the array;

FIG. 3C is a view in partial horizontal section of a longitudinal defect transducer within the array;

FIG. 4 is a partial block diagram of the ultrasonic testing system showing the electronics within the head unit as connected by umbilical cable to the receiver section of the control console;

FIG. 5 is a continuation of the system block diagram of FIG. 4 showing the microprocessor and the gating, averaging, alarm and indicator sections of the control console;

FIG. 6 is a schematic wiring diagram of a single pulser/pre-amp circuit, four of which are illustrated in FIG. 4; and FIG. 7 is a schematic diagram of a single pulser preamp circuit, a plurality of which are illustrated in FIG. 6.

DETAILED DESCRIPTION OF THE INVENTION

Figure 1:
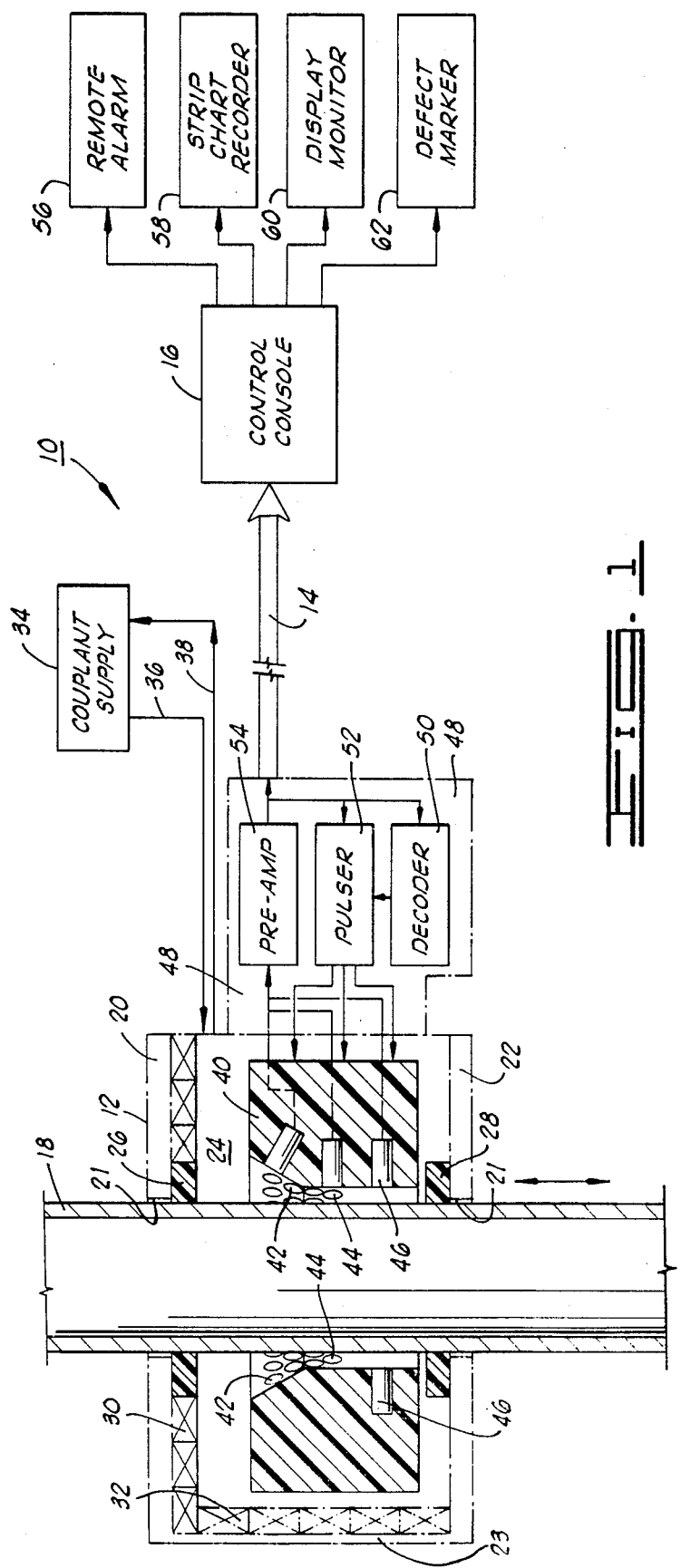
FIG. 1 is a block diagram with parts shown in section of the basic ultrasonic test head unit within the couplant frame as interconnected with the control console.

Referring to FIG. 1, an ultrasonic inspection system 10 consists of a test head unit 12 in connection via cable 14 to a control console 16. The test head unit 12 is suitably mounted at the test site for testing of tubular goods specimens such as pipe 18. Thus, and as more fully developed in applicant's co-pending application Ser. No. 242,833, in one form of application, the test head units 12 may be supported below or above a drilling rig platform in operative testing position during drilling and tripping operations. However, the system may be utilized in diverse surrounds for testing of numerous types of tubular goods.

The test head unit 12 is comprised essentially of an outer metal couplant frame, e.g. aluminum, consisting of an upper plate 20, lower plate 22 and suitable water proof side plates 23. The central passage 21 is provided through upper and lower plates 20 and 22, and the resilient sealing means 26 and 28 serve to retain couplant while aligning the pipe 18, as fully set forth in the co-pending application Ser. No. 242,833. In addition, it has been found that an acoustically insulative damping member placed within the upper extremity of the couplant fluid 24 serves to greatly reduce extraneous couplant mechanical compression wave noise as picked up by the pulsers and eventually transmitted in the RF content to control console 16. Thus, a panel of vulcanized horsehair matting 30 is secured across the upper extremity of the fluid chamber or couplant 24 when test head unit 12 is used in the vertical testing attitude and, alternatively, if unit 12 is used in the horizontal testing mode then an insulative matting 32 would be suitably disposed along the uppermost surface of couplant chamber 24.

Circulation of suitable couplant, such as pre-lube, synthetic oil or the like, under low pressure is provided from a suitable couplant supply 34 through circulation lines 36 and 38 to the couplant chamber 24. The couplant may be heated and thermostatically maintained at supply 34 thereby to enable more effective all weather usage. A transducer array 40, including a circumferal array of transverse transducers 42, longitudinal transducers 44 and the quadrature arrayed thickness transducers 46, is suitably supported generally centrally within the couplant chamber 24 in operative alignment with axial ports 21. Transducers 42, 44 and 46 are conventional ultrasonic transducers, e.g. lead titanate.

As will be further described, the transducer array 40 is effectively supported within a rigid frame (see FIG. 2) which also defines a pair of waterproof circuit chambers 48 on either side of array 40. The chambers 48 as disposed on opposite sides of array 40 provide space for clip-in mounting of a plurality of pre-amp/pulser and decoder printed circuit boards which function to control the respective transducers in each half of array 40. Thus, in each half of array 40 which would include twenty transverse transducers 42, twenty longitudinal transducers 44, and two thickness transducers 46, the respective chamber 48 would include a decoder board 50 (FIG. 1) and two pulser/pre-amp boards 52-54 in coactive interconnection with their respective transducers.

Incoming sync signal as well as decoder buss information and the RF signal output information are transmitted via umbilical cable 14 back to the control console 16 wherein the sequential multiplex signal information is processed and analyzed for output to provide display indication. Thus, an output is provided for actuating a remote alarm 56 and additional outputs are provided to a strip chart recorder 58 as well as a display monitor 60, e.g. a real time oscilloscope. Certain defect indications are also utilized to actuate a solenoid driven defect marker 62 which provides an optically discernible mark on the test specimen.

FIGS. 2 and 3 illustrate a particular form of array 40 as presently constructed to provide full circumferal coverage of an entire range of pipe diameters, e.g. 3½"

OD to 6⅝" OD, to provide indication of all transverse and longitudinal defects as well as wall thickness. The array 40 is supported in two separable half sections by rigid frame members 50 and 52 which define respective opposite board housing chambers 48. The opposite halves of array 40 are sealingly secured within the respective frame members 50 and 52 as respective Delrin seals and sealing rings 54 and 56 are secured around the upper circumfery. Circuit board chambers 48 are sealingly secured by Delrin seals 58 and 60 as secured by respective cover plates 62 and 64. A suitable latch or hinge mechanism 66 and 68 provides attachment of the array frame members 50 and 52, and opposite side plates 70 and 72 provide mounting affixure within test head unit 12.

The particular transducer array 40 is constructed with eighty defect transducers 42 and 44 and four quadrature-arrayed wall thickness transducers 46 disposed therebelow. Referring also to FIG. 3A, an upper bevel surface 74 is formed at an angle of 19.75 degrees to the array axis of inner diameter wall 76 and forty transverse defect transducers 42 are rigidly secured therebout, each radially aligned relative to the inner diameter of array 40 but directing energy at an angle of 19.75 degrees relative to the radius of array 40. Thus, as shown in FIG. 3B, reverberating acoustic energy within the wall of the test specimen 18, i.e. between the inner and outer diameter walls, will move upward with progressive lesser power reflections so that sensed energy will indicate homogeneous discontinuities lying transverse to the tubular goods axis.

Upper and lower rows of transverse transducers 42 are provided with twenty equally-spaced transducers each disposed in equal overlap so that the entire circumferal tube surface passing therethrough will receive ultrasonic energy input. Referring again to FIGS. 2 and 3A, the two rows of transverse transducers 42 are numbered sequentially progressing from No. 1 clockwise through Nos. 20 and 21 to terminate at No. 40. Under control of the associated pulser boards 52 (FIG. 1), the transverse transducers 42 are pulsed in pairs, each pair being displaced exactly ninety degrees in the array. Thus, the transducer pulsing sequence is as follows: pulse No. 1 fires transducers 1 and 11, pulse No. 2 fires transducers 2 and 12, pulse No. 3 fires transducers 3 and 13, and so on through pulse No. 11 firing transducers 21 and 31, pulse No. 12 firing transducers 22 and 32, and, finally, pulse No. 20 firing transducers 30 and 40.

Referring to FIGS. 3A and 3C, longitudinal defect transducers 44 are disposed in two equally-spaced and equally offset or staggered rows immediately beneath the bevel surface 74 around the inner diameter of array 40. Thus, forty transducers 44 are disposed in equal offset two-row array and numbered similarly to the transducers 42, and each longitudinal transducer 44 is directed at a similar slant angle or offset of 0.8190 inches relative to the array radius. As shown in FIG. 3C, each successive transducer 44 is viewing at a desirable refractive angle within the interior of the specimen wall, i.e. between ID and OD, and traversing enough specimen wall area to define a longitudinally aligned defect or inhomogeneity in the material. Pulsing of the transducers 44 takes place in ninety degree displaced pairs with numbering and succession the same as that for the transverse transducers 42, as above described. The thickness transducers 46 are also pulsed in selected sequence and directed radially into the tubular goods wall to provide a wall thickness travel time indication for conversion to thickness output.

Referring now to FIG. 4, the left side transverse and thickness transducers 80 are connected via a plurality of pulser leads 82 to a pulser/pre-amp 84. The left transducers 80 include twenty transverse transducers 42 and two thickness transducers 46 and the pulser/pre-amp 84 is a printed circuit board including twelve pulser and pre-amplifier circuits and two operational amplifier circuits, as will be further described. Left longitudinal transducers 86 are connected through pulser leads 88 to a pulsar/pre-amplifier 90. In like manner, right transverse and thickness transducers 92 are connected to pulser leads 94 and pulser/pre-amplifier 96, and the right longitudinal transducers 98 are connected through pulser leads 100 to a pulser/pre-amplifier 102.

The left side transducers are pulsed under sequence controlled by a decoder 104 which receives address buss data input on line 106 from the sequence controller 108 (FIG. 5). The address data is contained on six pairs of leads $+A_0$ through $+A_5$, a conventional coding form, and decoder 104 responds to provide selective trigger outputs on select-trigger leads 110 and 112 to the respective pulser/pre-amps 84 and 90. Again in like manner, right side transducer firing is accomplished as a decoder 114 responds to address buss input on line 106 to provide firing output on trigger leads 116 and 188 to respective pulser/pre-amps 96 and 102.

A transducer firing voltage of positive 100 volts is generated at control console 16 and is transmitted via lead 118 through cable 14 for input to each of the pulser/pre-amplifiers 84, 90, 96 and 102. A +15 volt supply is provided by lead 120 through cable 14 and input to each of decoders 104 and 114 wherein it is to provide a regulated +12 volt source. Synch voltage, as generated in sequence controller 108, is output on lead 122 (FIG. 5) through cable 14 for input to each of decoders 104 and 114. Decoder 104 and 114 each provide a regulated +12 volt output on leads 124 and 126 to their respective pulser/pre-amplifiers 84, 124 and 96, 102. Transverse and thickness outputs in the form of an RF energy pulse are provided on respective leads 128 and 130 for conduction back through umbilical cable 14 for input to the transverse receiver 132 and thickness receiver 134. The right side transverse and thickness data is transmitted similarly via leads 136 and 138 for input to the transverse and thickness receivers 132 and 134. Left side longitudinal data from pulser/pre-amp 90 is conducted via line 140 through cable 14 for input to a longitudinal receiver 142, and right side longitudinal data from pulser/pre-amp 102 is communicated via lead 144 back to longitudinal receiver 142. Address buss data on line 106 is also applied to respective Trim Pot decoder circuits 146 and 148 which provide control outputs, respectively, to the transverse receivers 132 and 134, and the longitudinal receiver 142. Each of the receivers 132, 134 and 142 includes channel 1 and channel 2 inputs for left side and right side data respectively. The receivers amplify and rectify the incoming RF signals in selected sequence to provide a video output to thickness and amplitude analysis gate boards, as will be further described. The Trim Pot decoder 146, responsive to address buss 106, provides calibration input on leads 150 and 152 to the transverse receiver and thickness receiver, respectively. Similarly, Trim Pot decoder 148 provides calibration output on lead 154 to the longitudinal receiver 142. Video output from the receivers 132, 134 and 142 is present on respective leads 154, 156 and 158.

Referring now to FIG. 5, sequential transverse video data on lead 154 is applied to a transverse amplitude gate 160 as similar video outputs from leads 156 and 158 are applied to a thickness gate 162 and a longitudinal amplitude gate 164, respectively. Each of the transverse and longitudinal gates 160 and 164 consist of an identical type of peak amplitude detector, each of which is responsive in sequence to forty transducers, i.e. responsive to twenty pulser pre-amps with two transducers per pre-amp, to provide output of a gate pulse and an analog DC voltage corresponding to the maximum signal amplitude detected.

The thickness gate 162 contains four thickness channels that are actuated sequentially to detect a minimum detected thickness during a frame interval. At the end of the frame, the minimum thickness value is transferred to a sample and hold register for output of an analog signal proportional to the detected minimum thickness. Transverse amplitude gate 160 provides a transverse threshold voltage on lead 166 and a transverse indication on lead 168 for conduction to the interface and strip chart recorder 170. A flaw detection output is also applied on a lead 172 for input to a transverse counter 174. Interconnect 176 provides frame set and reset data between sequence controller 108 and transverse amplitude gate 160. The longitudinal amplitude gate 164 includes similar outputs of a flaw detect pulse output on lead 178 to a longitudinal counter 180, and a longitudinal threshold signal on lead 182 and longitudinal data output on lead 184 as both are applied to interface and strip chart 170. Frame set and reset data is applied from sequence controller 108 via lead 186.

The thickness gate 162 provides a thickness output on a lead 188 to a thickness alarm counter 190, and it also provides a TOO THIN output on lead 192 to a thickness warning counter 194. Thickness threshold and thickness voltage are output on respective leads 196 and 198 to the interface and strip chart 170, and frame set and reset is interconnected on line 200 from sequence controller 108. The thickness voltage output on lead 198 is also applied to a thickness meter 202 which may be such as a digital meter reading out thickness in thousandths of an inch.

The interconnects 204 between sequence controller 108 and each of the counters 174, 190, 194 and 180 control outputs and inputs as each of the counters functions as an averager board in very close functional relationship to the sequence controller 108. Thus, the counters can essentially be considered an extension of the operation control of the sequencer. Such functional operations include: Averaging counters; Averaging counters load point select switches; Driving the signal lines to the test head unit 12; Channel decoding of the programmable read only memory in sequence controller 108; Channel decoding to route selected control pulses to the gate circuits 160, 162 and 164; and, providing gate termination. Additional interconnects 206 connect each of the counters 174, 190, 194 and 180 to the alarm latch and drivers board 208 which, in turn, may provide selected outputs to alarms, annunciators, defect markers and the like (not specifically shown). Instantaneous operator surveillance may be aided by synch output from sequence controller 108 via line 210 to a monitor 212, an oscilloscope or similar recorder, that may receive selected video and timing inputs 214.

Referring now to FIG. 6, the pulser/pre-amp 84 is shown in greater detail including a plurality of twelve individual pulser pre-amp circuits as they receive input from select-trigger interconnection 110 and connect to the left transverse and thickness transducers 80 (FIG. 4) by means of the pulsing connections 82. Received transducer output from connections 82, and as processed in the individual pre-amplifiers, is then output through a diode bank and operational amplifier output to the leads 128 and 130 (cable 14) for conduction back to the control console 16. Thus, FIG. 6 represents but a single pulser/pre-amp 84 as utilized with the left transverse and thickness transducers 80 for control of 20 transverse transducers and two thickness transducers as an amplified thickness video output is sequentially generated through op-amp 220 for conduction on lead 130, while sequentially pulsed transverse transducer outputs are processed through op-amp 222 for output on lead 128.

The pulser/pre-amp 84 receives input from decoder 104 (FIG. 4) of twelve SELECT inputs 224 and twelve TRIGGER inputs 226 as generated in decoder 104 to sequence transducer pulsing. The pulser/pre-amp 84, includes a plurality of pulser pre-amp circuits 84-1, 84-2, 84-3 and so on to pulser pre-amp circuit 84-12. The pulser/pre-amp 84 is connected so that pulser pre-amps 84-1 and 84-2 control the left side thickness transducers and pulser pre-amps 84-3 through 84-12 control the left side transverse transducers. The pulser/pre-amp 96 would be similarly wired to handle the right transverse and thickness transducers 92 (see FIG. 4). A similar circuit board is utilized at pulser/pre-amp 90 and would be wired with only ten individual pulser pre-amp circuits to control the twenty left longitudinal transducers 86, and the pulser/pre-amp circuit board 102 would be similarly wired to control the right longitudinal transducers 98.

As previously stated, a preferred sequence of firing may be as follows:

| SEQUENCE | ACTIVE TRANSDUCERS |
|---|---|
| 1 | Thickness 1L |
| 2 | Thickness 2L |
| 3 | Thickness 3R |
| 4 | Thickness 4R |
| 5 | Transverse 1 and 11 |
| 6 | Transverse 2 and 12 |
| 7 | Transverse 3 and 13 |
| . | . |
| . | . |
| 14 | Transverse 10 and 20 |
| 15 | Transverse 21 and 31 |
| 16 | Transverse 22 and 32 |
| . | . |
| . | . |
| 24 | Transverse 30 and 40 |
| 25 | Longitudinal 1 and 11 |
| 26 | Longitudinal 2 and 12 |
| 27 | Longitudinal 3 and 13 |
| . | . |
| . | . |
| 34 | Longitudinal 10 and 20 |
| 35 | Longitudinal 21 and 31 |
| 36 | Longitudinal 22 and 32 |
| . | . |
| . | . |
| 43 | . |
| 44 | Longitudinal 30 and 40 |

Each pulser pre-amp 84-n actuates a respective pulsing lead 82 which is connected in parallel to actuate a selected pair of transducers. Thus, in the case of pulser/pre-amp 84, pulsar pre-amp 84-1 is actuated to energize pulsing line 82-1 to fire the No. 1 left thickness transducer which returns signal energy processed through the pre-amp portion with output indication provided on lead 228 through a diode 230 for amplification in op-amp 220 and RF indication output on lead 130 to control console 16. In like manner, pulser pre-amp 84-2 energizes pulser line 82-2 to the remaining left thickness transducer and return energy is amplified with output on lead 232 through diode 234 and op-amp 220. As sequencing recommences through the left side tranducers, SELECT and TRIGGER inputs actuate pulser pre-amp 84-3 to energize pulsing lead 82-3 and transverse transducers 1 and 11 with subsequent signal return amplified and output on a lead 82-3 through a respective diode 236-3 for output through op-amp 222 and RF lead 128 to control console 116. Thus, sequential energization of the pulser/pre-amps 84, 90, 96 and 102 function to effect transducer energization and received signal processing through all eighty-four transducers in the circumferential array.

FIG. 7 illustrates schematically an individual pulser preamp circuit, e.g. pulser pre-amp 84-1 and the attendant input and output connections. The pulser portion of the circuit centers around an SCR 240, Type GA301, having a common connected plate, a cathode connected to a junction 242 and having a gate electrode connected through a resistor 244 to the trigger input 226-1. The junction 242 is connected through a load resistor 246 to the +100 volt supply lead 118 as well as through a capacitor 248 and junction 250 to a tuned output circuit. The junction 250 is connected through a tuning coil 252 to the regulated +12 volt supply lead 124, and junction 250 is also connected to the plate of a diode 254 having its cathode connected to a junction 256 which provides parallel output through tuning resistors 258 and 260 to the pulsing leads 262 and 264, i.e. pulsing lead pair 82-1. Thus, trigger input to SCR 240 develops a high voltage pulse at junction 242 to energize oscillation as developed at junction 256 to provide parallel pulsing output for energization of a select pair of transducers. Inductance 252 and capacitor 248 provide an L-C circuit for setting the frequency of oscillation. In present operation, the thickness transducers are pulsed at 5.0 MHz while the transverse and longitudinal transducers are each pulsed at a frequency of 2.25 MHz.

The return low level signal as received back from the transducers through junction point 256 on lead 266 for amplification in solid state amplifier 268, a Type 3N211, to provide a return signal output at a junction 270. The amplification factor of device 268 is controlled by the setting of trim potentiometer 272 connected between ground and the regulated 12 volt input. Passive elements, i.e. inductance 274 and common-connected capacitor 276, filter the low level received transducer signal as seen at junction 278 for input to selection and pre-amplification circuitry consisting of NPN transistors 280 and 282, Type 2N4401. Transistor 280 is connected with the collector energized by the 12 volt regulated supply on lead 124 and the input SELECT pulse on lead 224-1 is applied to the base. A positive-going signal on the base enables conduction of transistor 280 and energization of amplifier transistor 282 and transducer return signal present on the base (junction 270) is amplified to provide output transducer signal on lead 228. The inductance 274 and capacitance 276 will vary in accordance with the particular frequency of operation, i.e. selection at 2.7 MHz uses a 100 microhenry inductance and a 30 picafarad capacitance while operation at 5 MHz utilizes a 47 microhenry inductance and a 10 picafarad capacitance. The output signal on lead 228 is then applied through an output diode, e.g. 230 of FIG. 6, for input to the summing amplifier or op-amp 220 and output on lead 130. The summing operational amplifiers serve to drive the amplified return signal over the extended length cable 14 to the receiver units at the control console.

In operation, the test head 12 may be located horizontally or vertically in a selected test position and the control console 16 is connected via cable 14 from any suitable operating position. In the case of an industrial manufacturing application, the control console 16 may be placed conveniently near the specimens and testing station, proximity not being a particular factor. In such as an oil field application, and as used for testing vertical tubular goods during tripping operations, it is desirable to place the test head unit 12 in position above or below the rig floor with the drill string or tubing complement passing therethrough while the control console 16 may be located at a removed position that is more conducive to operator control and surveillance. The ability to locate the control console at considerable distances is also desirable from the hazard-proof standpoint, such as may be encountered on offshore drilling stations, since the electrically conductive components of test head unit 12 are in an immersed disposition while the hot components of control console 16 may be located at a safe, hazard-free position having no likelihood of explosive potential.

The test head unit 12 includes the acoustic insulator matting 30 at the upper extremity of the couplant chamber 24 and this serves very effectively to remove extraneous acoustic return signals that are sometimes of highly interfering nature. In addition, couplant may be continually supplied to chamber 24 from supply 34 as the specimen under test or pipe 18 may be freely moved through test head unit 12 at considerable axial speeds without rotation as ultrasonic testing of the circumferal surface is effected for thickness as well as longitudinal and transverse defects. The circumferential disposition and angular seating of the transducer array 40 is such that each of the transverse and longitudinal transducer groups provide complete circumferential coverage of the tubular goods. Further, while the array 40 has the capability of completely testing the circumference of a wide range of tubing OD sizes at high speed without rotation, each of the transverse and longitudinal transducers 42 and 44 and the thickness transducer 46 is potted within array 40 in a permanent, non-adjustable seating. The body of transducer array 40 may be formed of suitable plastic such as Delrin, or, alternatively, it is contemplated that the transducer array be formed from aluminum.

The transducers within array 40 are sequentially energized in pairs to emit pulsed ultrasonic energy at the requisite frequency and to receive any return energy for preamplification and processing through the receiver to identify defects. Sequential pairs pulsing is controlled by the sequence controller 108 (FIG. 5) and the data on synch output line 122 and address buss 106 through umbilical cable 14. The thickness transducers 46 are interrogated first, and if no thickness reading registers then the system will not continue with interrogation of the remaining channels as it re-energizes thickness transducers 46 until a valid thickness reading is obtained. Upon occurrence of a no-thickness reading, visual and audible alarm is made. When a valid thickness has been obtained, the strip-chart 58 and thickness meter 202 are updated with the thinnest measurement obtained, flaw thresholding is carried out, and the sequence control 108 increments to the transverse channel for next analysis.

The twenty pairs of transverse transducers 42 are then interrogated as the respective pulser/preamps are energized to pulse sequential pairs while the sequential outputs are conducted back through the respective transverse receiver 132. Output from the receiver 132 of received flaw energy is supplied through the transverse amplitude gate 160 which measures the peaks within a pre-selected gate time, and retrieves only the largest peak output from all of the transverse preamplifiers in that particular peripheral sequence. The value of the largest peak output is threshold detected and the output is applied to the strip-chart recorder 58 as well as the other output display equipment. Results of the threshold detection through the transverse peak detection are conducted back to the sequence controller 108 which performs a channel averaging function as it functions in coaction with transverse counter 174. The averaging counters provide the system with the capability of not allowing extraneous noise spikes to trigger an alarm condition as the system can then positively identify the presence of a flaw that exceeds the preset threshold limits.

The sequence controller 108 then functions to energize the pulser/preamps for twenty pairs of longitudinal transducers 46. Each of the respective pulser/preamps is sequentially pulsed and returned energy is applied through the longitudinal receiver 142 and detected peak outputs are input to the longitudinal amplitude gate 164. Here again, the amplitude gate 164 measures detected peaks within a selected gate window and retains only the largest peak output from all preamps for the particular peripheral sequence of energization. The value of the largest peak is then compared with the pre-set threshold, and the compared output is applied through the sequence controller 108 for performance of the longitudinal count averaging function within longitudinal counter 180. Peak output values are also applied to the stripchart recorder 58, display monitor 60, etc. Sequence controller 108 then cycles through the next following routine beginning with the thickness channel interrogation.

The foregoing discloses a novel ultrasonic testing system that is particularly adaptable for use with tubular goods. The system has a circumferal ultrasonic testing array which utilizes a plurality of pulse/echo transducers to provide complete circular surface coverage of an axially moving but non-rotating pipe or tubular member. The array of the system has the further capability of examining tubular stock at relatively high axial speeds and is able to accommodate a wide range of outside diameter sizes with permanently seated transducers within the circular array. Such permanently disposed transducers within a non-contacting circular array serve to enable particular applications such as on-site testing of oil field tubular goods at the drilling rig floor and similar testing of tubular goods in their practical working environment.

Changes may be made in combination and arrangement of elements as heretofore set forth in the specification and shown in the drawings; it being understood that changes may be made in the embodiments disclosed without departing from the spirit and scope of the invention as defined in the following claims.

What is claimed is:

1. Apparatus for ultrasonic testing of tubular goods, comprising:
   circular array means defining a central bore for receiving said tubular goods, and having a plurality of ultrasonic transducers each rigidly secured in said array means and directed at a predetermined angle relative to the radius of the central bore;
   frame means supporting array means and having at least one fluid-tight chamber;
   test head means supporting said frame means and maintaining a fluid couplant in surround of said array means and the proximate portion of said tubular goods;
   pulser means secured in said fluid-tight chamber and connected to said array means to energize said transducers;
   amplifier means secured in said fluid-tight chamber and connected to said array means to receive output from said transducers; and
   means controlling said pulser means and amplifier means for sequentially energizing selected transducers and sequentially receiving return signals to indicate defects in said tubular goods.

2. Apparatus as set forth in claim 1 wherein said means controlling comprises:
   decoder means secured in said fluid-tight chamber and connected to said array means and time sequentially controlling said pulser means and amplifier means; and
   control means connected to said decoder means and receiving said return signals from said amplifier means.

3. Apparatus as set forth in claim 2 wherein:
   said control means is disposed at a removed location from said tubular goods and test head means.

4. Apparatus as set forth in claim 1 which further includes:
   a second plurality of transducers, each rigidly secured in said array means and directed at a second predetermined acute angle relative to the radius of the central bore.

5. Apparatus as set forth in claim 4 wherein:
   said plurality of transducers are aligned for detection of transverse defects; and
   said second plurality of transducers are aligned for detection of longitudinal defects.

6. Apparatus as set forth in claim 4 which is further characterized to include:
   a third plurality of transducers, each rigidly secured in said array means and directed radially relative to the central bore.

7. Apparatus as set forth in claim 6 wherein:
   said plurality of transducers are aligned for detection of transverse defects;
   said second plurality of transducers are aligned for detection of longitudinal defects; and
   said third plurality of transducers are aligned for detection of tubular goods wall thickness.

8. Apparatus as set forth in claim 7 wherein:
   said array means is separable into two semi-circular halves.

9. Apparatus as set forth in claim 1 wherein said pulser means comprises:

a plurality of pulser circuits each connected for energization of at least one selected transducer.

10. Apparatus as set forth in claim 9 wherein said amplifier means comprises:
a plurality of amplifier circuits each connected to receive output from at least one selected transducer.

11. Apparatus as set forth in claim 1 wherein:
said array means is separable into two semi-circular halves.

12. An apparatus for ultrasonic testing of tubular goods moving axially without rotation, comprising:
a test head secured in position to have said tubular goods moved axially therethrough;
frame means supported by said test head, said frame means having a circular array means to receive said tubular goods, and having at least one fluid-tight chamber adjacent said array means;
plural ultrasonic transducer means secured within said array means and surrounding said tubular goods in equi-spaced disposition;
circuit means secured within said frame means fluid-tight chamber for controlling ultrasonic energy generation and received energy returned signal output;
fluid couplant supply means continually supplying fluid couplant to said test head to provide envelopment of said transducer means, frame means, and proximate portion of tubular goods;
control means disposed remotely from said frame means; and
multiconductor means connecting said frame means and control means.

13. An apparatus as set forth in claim 12 which is further characterized to include:
a line of acoustic insulative material at least covering the inner, uppermost extremity of said test head means in contact with said fluid couplant.

14. An apparatus as set forth in claim 13 wherein:
said acoustic material is a rubberized horse hair matting.

15. An apparatus as set forth in claim 12 wherein said ultrasonic transducer means comprises:
a first circumfery of transducers aligned at an acute angle to the radius of said circular array means for transverse defect detection;
a second circumfery of transducers aligned at a second acute angle to the radius of said circular array means for longitudinal defect detection; and
a plurality of transducers directed radially to detect tubular goods wall thickness.

16. An apparatus as set forth in claim 12 wherein said circuit means comprises:
pulser means enabled from said control means to energize said transducer means; and
amplifier means receiving return signal from said transducer means and providing return signal output to said control means.

17. A test head for ultrasonic testing of tubular goods, comprising:
a circular array of ultrasonic transducer means defining a test bore;
an array frame supporting said circular array and defining a sealed, fluid-tight chamber adjacent said array;
circuit means including a pulser and pre-amplifier disposed within said sealed, fluid-tight chamber;
frame housing means supporting said array frame generally centrally and having wiper sealed acess holes in alignment with said test bore; and
means supplying liquid couplant within said housing means in envelopment of said array frame and the proximate portion of tubular goods.

18. A test head as set forth in claim 17 which is further characterized to include:
a panel of acoustic insulating material secured throughout the upper extremities within said frame housing means.

* * * * *